(12) United States Patent
Hasenoehrl et al.

(10) Patent No.: US 8,518,001 B2
(45) Date of Patent: Aug. 27, 2013

(54) SKIN TREATMENT DEVICE

(75) Inventors: Erik John Hasenoehrl, Loveland, OH (US); Keith David Fanta, Middletown, OH (US); Helen Rochelle Kemp, Glendale, OH (US); Aleksey Mikhailovich Pinyayev, West Chester, OH (US); John Andrew McDaniel, Middletown, OH (US); Paul John Edward Vernon, Hamilton, OH (US); Paul Robert Tanner, Lebanon, OH (US); Linda Eva Cortina, Mason, OH (US); Nancy Lorincz Leppla, Loveland, OH (US); Dean Arthur Zimmerman, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 751 days.

(21) Appl. No.: 12/139,093

(22) Filed: Jun. 13, 2008

(65) Prior Publication Data

US 2009/0124985 A1   May 14, 2009

Related U.S. Application Data

(60) Provisional application No. 60/934,439, filed on Jun. 13, 2007.

(51) Int. Cl.
*A61M 35/00*       (2006.01)
*A61H 15/00*       (2006.01)
(52) U.S. Cl.
USPC ............................ 604/289; 601/112; 606/131

(58) Field of Classification Search
USPC .......................................... 604/289; 606/131
See application file for complete search history.

(56) References Cited

U.S. PATENT DOCUMENTS

| 578,195 | A | | 3/1897 | Beatty |
| 3,092,111 | A | * | 6/1963 | Saperstein et al. ............ 606/131 |
| 3,616,015 | A | | 10/1971 | Kingston |
| 3,949,137 | A | * | 4/1976 | Akrongold et al. ........ 15/104.93 |
| 4,397,755 | A | | 8/1983 | Brierley |
| 4,426,422 | A | | 1/1984 | Daniels |
| 4,548,857 | A | | 10/1985 | Galante |
| 4,652,391 | A | | 3/1987 | Balk |
| 4,664,248 | A | | 5/1987 | Goodman |

(Continued)

FOREIGN PATENT DOCUMENTS

| DE | 2754189 A1 | 10/1979 |
| EP | 050887 | 5/1984 |

(Continued)

OTHER PUBLICATIONS

PCT Search Report, PCT/US2008/066910, Jun. 13, 2008; 16 pages.

*Primary Examiner* — Susan Su
(74) *Attorney, Agent, or Firm* — S. Robert Chuey

(57) ABSTRACT

A personal skin polishing or microdermabrasion device having a convenient form factor with a applicator attached to a contoured housing with a handle portion. The housing contains a battery, a cordless motor and a gear box to provide an appropriate rotational velocity to the output shaft that is coupled to the applicator. The applicator may be a foam material selected to cushion the skin from excessive abrasion to the particles in a personal care composition to be used with device, and to have a porosity that will enable the foam to interact with the particles and enhance the skin polishing effect.

15 Claims, 15 Drawing Sheets

(56) References Cited

U.S. PATENT DOCUMENTS

| | | | |
|---|---|---|---|
| 4,709,798 A | 12/1987 | Herzog | |
| 4,788,883 A * | 12/1988 | Hashizume | 74/570.2 |
| 4,884,678 A | 12/1989 | Graham | |
| 5,117,993 A | 6/1992 | Vesborg | |
| 5,143,722 A | 9/1992 | Hollenberg | |
| 5,479,762 A | 1/1996 | Bliss | |
| 5,484,052 A | 1/1996 | Pawloski | |
| 5,564,551 A | 10/1996 | Schmitt | |
| 6,079,546 A | 6/2000 | Sala | |
| 6,108,869 A | 8/2000 | Meessmann | |
| 6,176,369 B1 | 1/2001 | Petrovic | |
| 6,209,708 B1 | 4/2001 | Philipp | |
| 6,283,336 B1 | 9/2001 | Dwyer | |
| 6,294,179 B1 | 9/2001 | Lee | |
| 6,796,352 B1 | 9/2004 | Geurtsen | |
| D502,603 S | 3/2005 | Seifert | |
| 6,893,717 B1 | 5/2005 | Tsai | |
| D507,114 S | 7/2005 | Seifert | |
| D518,643 S | 4/2006 | Kling | |
| 7,166,279 B2 | 1/2007 | Law | |
| 7,179,152 B1 * | 2/2007 | Rhoades | 451/41 |
| 2004/0015139 A1 * | 1/2004 | La Bianco et al. | 604/289 |
| 2004/0123955 A1 | 7/2004 | Kramer | |
| 2004/0161402 A1 * | 8/2004 | Brooks et al. | 424/70.15 |
| 2005/0203575 A1 * | 9/2005 | Carson et al. | 606/204.35 |
| 2006/0021033 A1 | 1/2006 | Huynh | |
| 2006/0058714 A1 | 3/2006 | Rhoades | |
| 2006/0130335 A1 | 6/2006 | Suen | |
| 2006/0200099 A1 * | 9/2006 | La Bianco et al. | 604/289 |
| 2006/0289025 A1 * | 12/2006 | Nevakshonoff | 132/73.6 |
| 2007/0293795 A1 * | 12/2007 | Carroll | 601/138 |
| 2008/0051692 A1 * | 2/2008 | Petersen et al. | 604/20 |
| 2009/0118684 A1 * | 5/2009 | Da Silva et al. | 604/290 |

FOREIGN PATENT DOCUMENTS

| | | |
|---|---|---|
| EP | 0179264 | 10/1988 |
| EP | 0257458 | 3/1989 |
| EP | 0571193 | 9/1999 |
| FR | 2595249 | 12/1989 |
| GB | 1355654 A | 6/1974 |
| GB | 2140451 | 12/1986 |
| GB | 2181738 | 6/1990 |
| JP | 60006795 | 1/1985 |
| JP | 60108499 | 6/1985 |
| JP | 11139543 A | 5/1999 |
| JP | 11157635 A | 6/1999 |
| JP | 2006089093 A | 4/2006 |
| JP | 2006160416 A | 6/2006 |
| WO | WO2004098616 | 11/2004 |
| WO | WO2006130643 | 12/2006 |

* cited by examiner

SKIN TREATMENT DEVICE

CROSS REFERENCE TO RELATED APPLICATION

This application claims the benefit under 35 USC 119(e) to U.S. Application No. 60/934,439, filed Jun. 13, 2007.

FIELD OF THE INVENTION

This application relates to a skin treatment device, a kit comprising the skin treatment device and a personal care composition, and method of using the device and kit.

BACKGROUND OF THE INVENTION

Skin treatments, particularly for facial skin, are legion and range from simple cleansing and moisturizing to more aggressive ways to rejuvenate the skin. One popular method of rejuvenation is microdermabrasion in which the outermost layer of skin, the stratum corneum, is removed with the end goal of reducing the appearance of fine lines, wrinkles and blemishes. Broadly microdermabrasion is the removal of the outer surface layer of skin by buffing with tiny rough particles. Sometimes microdermabrasion is referred to as skin polishing. Simply put microdermabrasion takes advantage of the body's tendency to heal itself. The two innermost layers of the epidermis are a new skin layer comprised of skin cells which are in the process of maturing, just beneath the stratum corneum which is the layer of dead skin cells that acts mostly as a barrier between the outside world and the lower skin layers. The stratum corneum allows only the smallest molecules to penetrate to the lower layers. As a result, only part of the moisture and nutrients from lotions and creams applied to the skin actually passes through the stratum corneum. The stratum corneum is also the layer where many minor imperfections such as fine wrinkles, blemishes and pigmentation reside. Microdermabrasion targets the stratum corneum by breaking up the dead skin cells. The body responds to the procedure as if there has been an injury to the skin and works to replace the lost skin cells with healthy new ones. This results in an improved appearance to the skin since newer skin cells look and feel smoother, and the imperfections that were in the stratus corneum are removed. An added benefit is that without the stratum corneum barrier, medicinal creams, nutrients and moisturizers are more effective because more of the active ingredients are absorbed and penetrate to the lower layers of skin.

Microdermabrasion that is performed by professionals in a dermatology practice, clinic or spa is generally done with a specialized tool that shoots a stream of tiny crystals at the skin and collects the leftover skin cells and used crystals with a vacuum. The vacuum action of a professional tool pulls a small section of skin into the tip of the device; causes a mild swelling to bring impurities to the surface; shoots the stream of crystals across the target skin patch and then collects the debris for disposal.

An alternative to the professional tool are microdermabrasion creams that can be used in the home. These creams can be applied by rubbing them onto the target area with the hands to push the particles against the skin to break up the dead cells of the stratum corneum. A number of personal microdermabrasion devices have been marketed to apply these creams. Such conventional personal skin treatment implements generally have a flat disk shaped applicator to apply the cream to the face. The flat disk applicators range from non-absorbent hard plastic material with a surface topography, to absorbent materials such as cloth or sponge material. These devices typically provide a vibratory motion to the disk applicator to work the particulate cream into the skin. A drawback of the flat disk applicator is its inability to reach all areas of the face, such as the concave contour between the nose and cheek, for example. Another drawback is the use of vibratory motion at the application locus. While vibratory motion does work the particulate cream into the skin to some degree, tests have shown that subjects have increased satisfaction with the action of a rotary motion applicator. Vibration and oscillation are not effective because the skin moves together with the particles and exfoliating surface, whereas for effective exfoliation the exfoliating surface and the particles must move relative to the skin.

SUMMARY OF THE INVENTION

The present invention is related to a skin treatment device. The device is suitable for a variety of skin treatments such as microdermabrasion, skin polishing and delivery of personal care composition (i.e., a composition suitable for topical application on mammalian keratinous tissue). The skin treatment device may be used with or without a personal care composition such as a cream, lotion, ointment, balm, serum, wax or like compounds.

In one embodiment, the present invention is in the form of a personal microdermabrasion skin treatment device having an applicator and a housing. The housing may have a narrowed neck and an elongated ovoid handle. The handle area may be designed to rest comfortably in the palm of a user's hand. Inside the housing is a battery with a cordless motor, a planetary gear box and its output shaft. The output shaft extends to the applicator attachment area to impart a rotational motion to an applicator tip mounted thereto. The rotational motion of the applicator against the skin which imparts a constant linear velocity parallel to the surface of the skin has been found to be more beneficial than a vibratory motion that is imparted both parallel and perpendicular to the skin.

The foam application may have a tapered conical shape enabling the user to thoroughly reach contoured areas of the face. The overall shape of the device enables the device to be handled in an intuitive and precise fashion for most users.

The skin treatment device is designed to be used alone or in conjunction with a personal care composition that may have particles admixed therein. The foam material for the applicator may be chosen to cushion the skin against excessive abrasive action of the particles, and to interact with the particles to hold them in the recesses in the foam's cell structure. The porosity and firmness of the foam material is selected with consideration of the sizes of abrasive particles contemplated to be used with the device to optimize the foam and particle interaction to thereby enhance the skin polishing effects of the device.

Another aspect of the invention is an internal mechanism that enables a segmented two-part applicator to counter-rotate thereby enhancing the skin polishing effect of the device. The mechanism includes a gear combination in which a pair of crown-type gears are disposed in opposing relation with their toothed surface facing one another. Meshed with the crown-type gears is a cross gear that enables the crown-type gears in stacked relation to rotate counter to one another. One crown-type gear drives the rotation of one of the parts of the applicator, and the other crown-type gear drives the rotation of the other part of the applicator in the opposite rotational direction. Yet another aspect of the invention is a skin treatment device employing a similar gear mechanism to transmit counter-rotational motion to two concentrically disposed skin treatment surfaces. The inner surface rotates in one direction and the outer surface rotates in the opposite direction.

Another aspect of the invention relates to a kit comprising the skin treatment device, the personal care composition, and/or replacement applicators. Other configurations, features and advantages of the invention will be, or will become, apparent to one skilled in the art upon examination of the following figures and detailed description. It is intended that all such additional systems, methods, features and advantages be included within this description, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views. In the drawings.

DETAILED DESCRIPTION OF THE INVENTION

Figure 1:
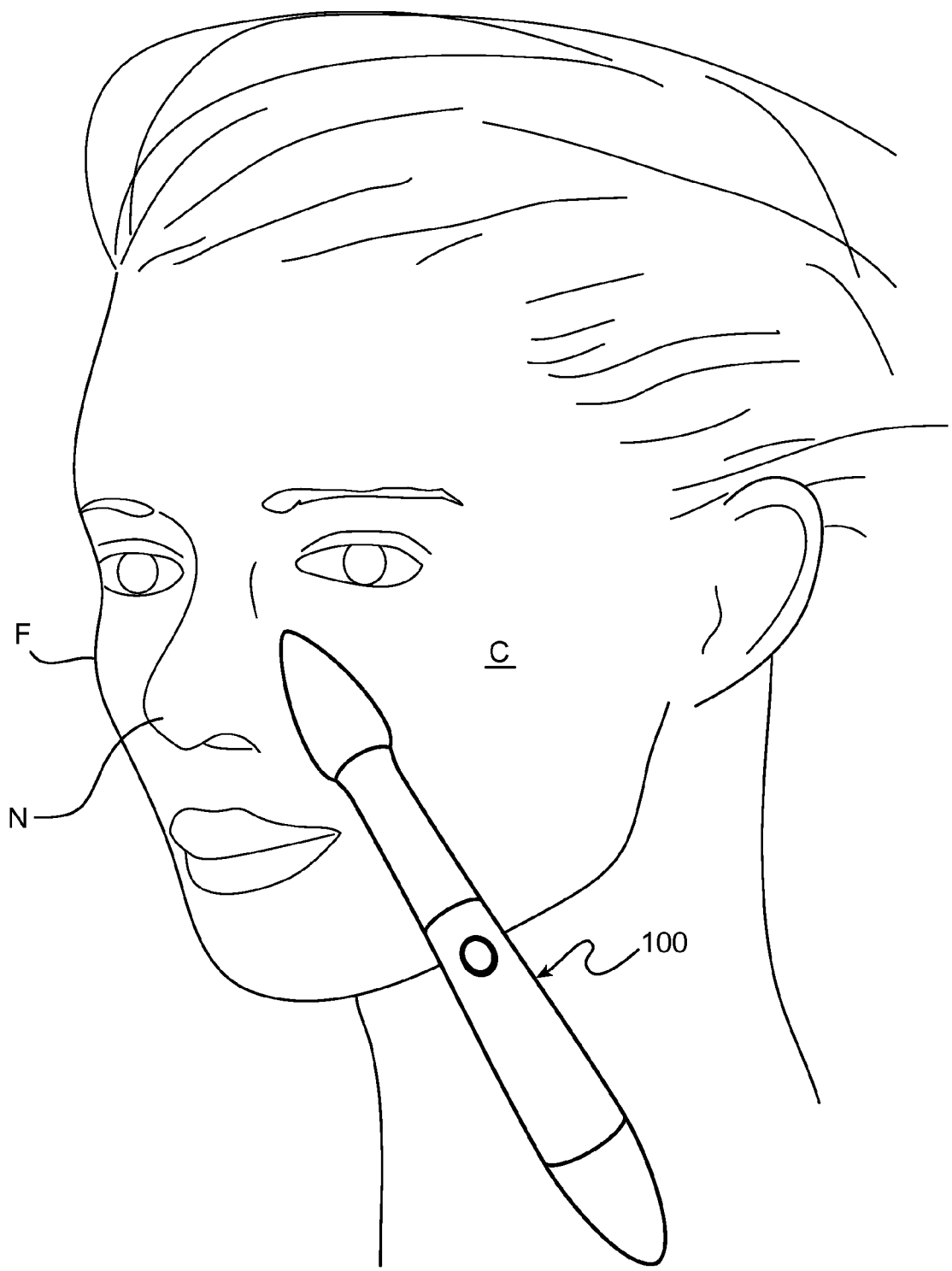
FIG. 1 is a schematic view of a skin treatment device in accordance with the present invention shown in position on a user's face.
Figure 2:
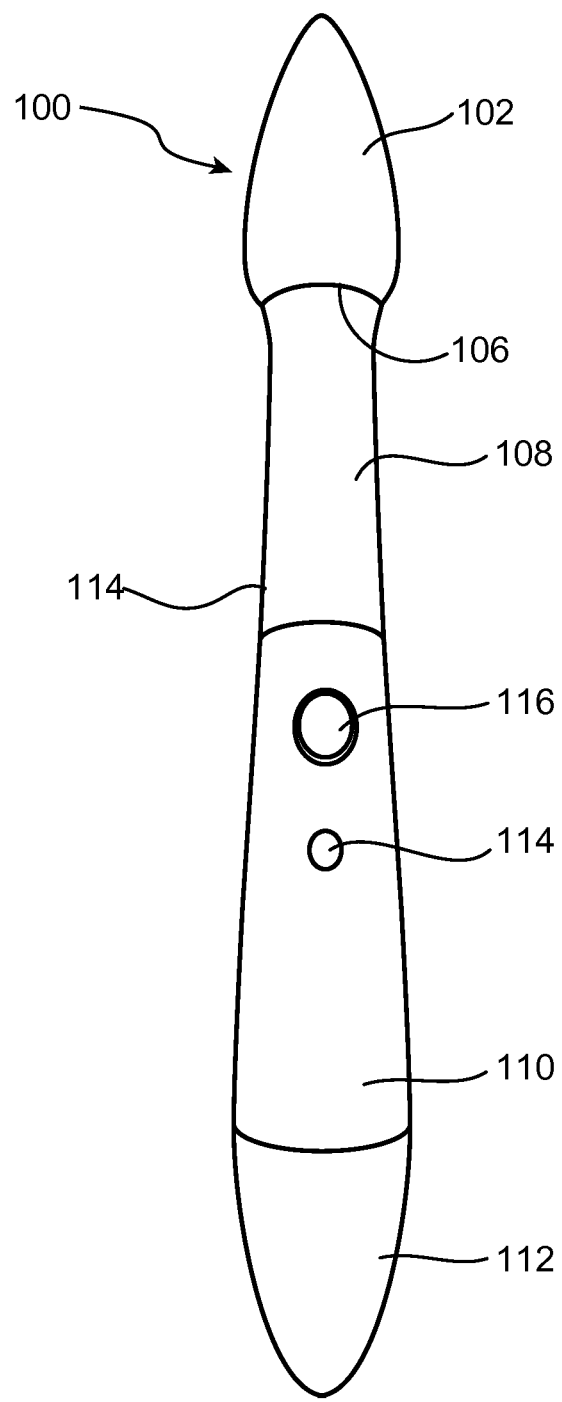
FIG. 2 is an elevational view of the skin treatment device.
Figure 3:
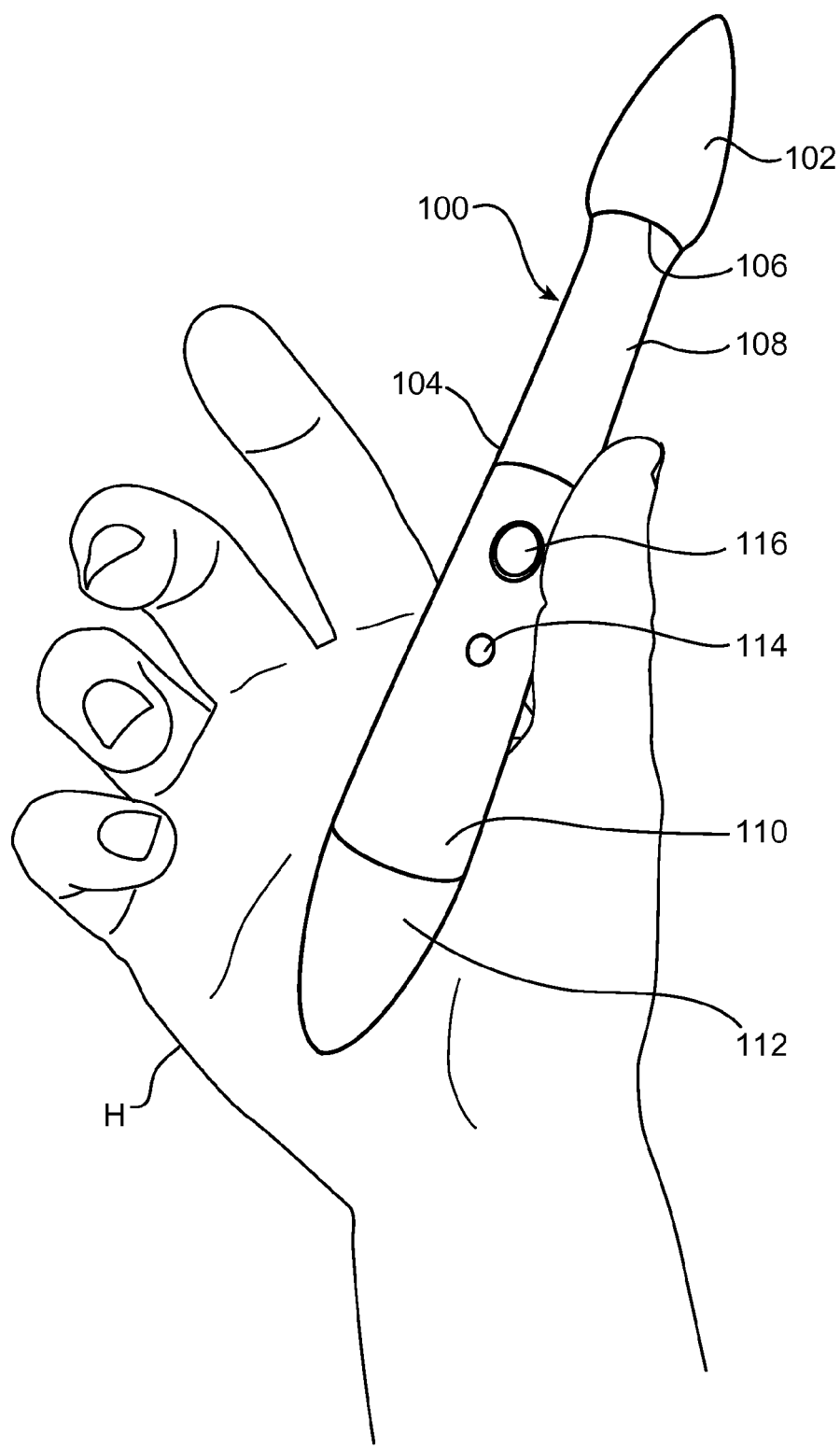
FIG. 3 is a perspective view of the skin treatment device shown in a user's hand.

One embodiment of a skin treatment device 100 is shown in FIG. 1 in a position to be used for treatment of the face F. Broadly, the external features of device 100 comprise an applicator 102 and a housing 104. In the embodiments shown in FIG. 2, housing 104 has a contoured shape ranging downward from applicator attachment 106, to a narrowed neck portion 108 to an elongated ovoid handle area 110. Housing 104 tapers outward from neck portion 108 to smoothly transition to ovoid handle area 110. As seen in FIG. 3, handle area 110 is configured to rest comfortably in the palm of a user's hand H so that narrow neck portion 108 is easily within reach of user's fingers to operate the controls. Housing 104 includes a housing cap 112. The ovoid shape of the handle area is formed by a combination of housing 104 and cap 112. Device 100 has an on-off switch 114 and an applicator ejection control 116 located along housing 104. With respect to FIGS. 1-9, for convenience of description the applicator end is sometimes referred to as the top, forward end or the front of the device, while the handle end is sometimes referred to as the bottom, the rearward end or the rear of the device. These descriptions to the orientation of the device as illustrated in the drawings are for convenience and clarity, and should not be interpreted as limiting the scope of the invention in any way. It is understood that directional adjectives will change if the device were held or handled in a different orientation than as pictured.

Figure 4:
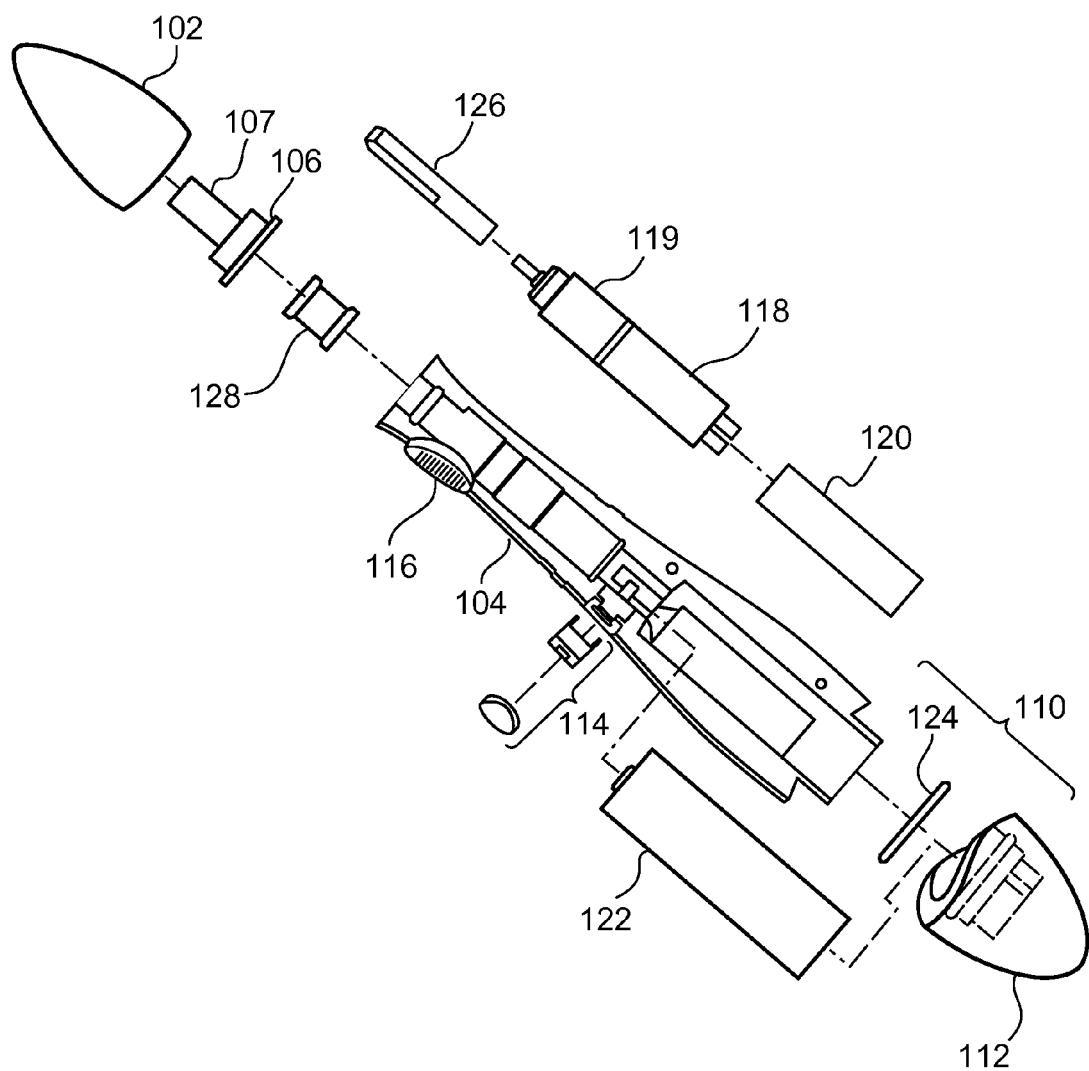
FIG. 4 is an exploded assembly view of the skin treatment device.

The internal structure of device 100 is shown in an exploded assembly view in FIG. 4. Inside housing 104 is a motor 118 operatively coupled to and controlled by a circuit on a printed circuit board, PCB 120. Motor 118 and PCB 120 are also operatively coupled to a battery 122. In the embodiment illustrated in FIG. 4, the motor is a cordless DC motor powered by a battery. The battery may be rechargeable. It should be recognized that the device 100 may be corded. As seen in FIG. 4, the PCB and battery are located toward the handle side of motor 118, with the motor and the battery being aligned. Also operatively coupled to PCB 120 near the junction between motor 118 and battery 122 is power switch 114 which has a soft-touch outer surface covering a detent-type power switch tied to the PCB 120. Downstream of battery 122, an o-ring seal 124 is inserted between housing 104 and cap 112 which are connected to one another by any known means such as a threaded connection as illustrated.

On the opposite end of motor 118 is a planetary gear box 119 that contains the necessary gears to provide the appropriate rotational velocity to an output shaft 126 that engages an internal portion of applicator attachment 106 to transmit the rotary motion of the motor's output to the applicator 102. Annularly placed around output shaft 126 is a free spinning hair guard 128 located just below the applicator attachment. Applicator attachment 106 has on its shaft portion 107 an element that enables the device to releasably engage applicator 102. This release element is operatively coupled to controller 116 so that the user can release or eject the attached applicator by actuating controller 116. In the illustrated embodiment, ejector control 116 is a slide mechanism that enables the user to eject the applicator 102. In certain embodiments, the applicator 102 and the applicator attachment 106 may be a unitary structure such that are jointly removable.

In certain embodiments, the device 100 may further comprise a reservoir disposed within the housing 104. The reservoir may be in liquid communication with the applicator 102. For example, the reservoir may be joined to the applicator by a conduit through which a liquid such as a personal care composition may flow. The conduit may extend through the applicator attachment 106 so that liquid may be dispensed into or on the applicator 102. The device 100 may include an actuator that is operatively joined to the reservoir and/or the conduit. The actuator is any device suitable for dispensing the liquid contained in the reservoir. The actuator may be a small pump. The actuator may be any simple mechanical device for applying pressure to the reservoir or to the liquid in the reservoir such as a piston.

Figure 5:
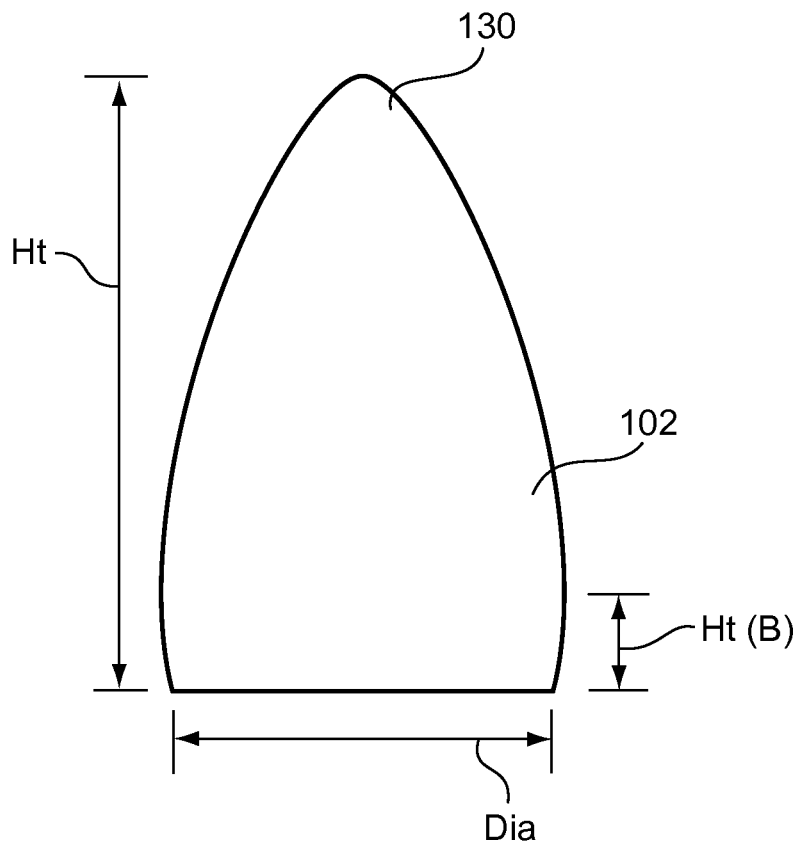
FIG. 5 is a detailed side view of the applicator.
Figure 6:
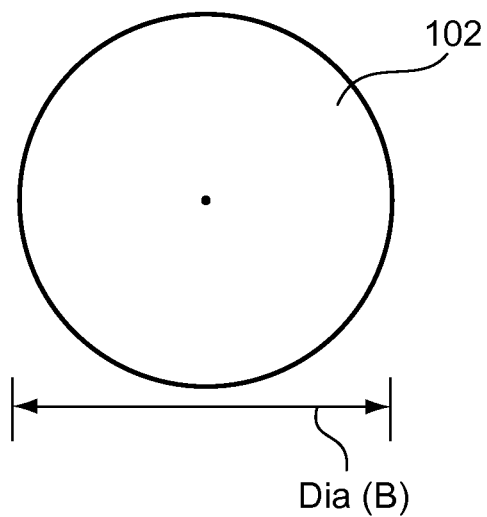
FIG. 6 is a detailed end view of the applicator.

Turning to FIGS. 5-6, the shape of applicator 102 is shown in detail. Applicator 102 has an overall conical shape. This shape enables the applicator to thoroughly reach contoured areas of the face such as the concave area between the nose and cheek. Pointed tip 130 also enables the user to place the applicator in even smaller areas such as the philtrum without irritating the more sensitive skin on the lips. In addition, the taper of applicator 102 enables more targeted microdermabrasion, polishing, or personal care composition delivery, and enables the user to get closer to the eyes without risking any injury to them or the surrounding tissue. The sides of the cone shape can be used to target larger areas of the face such as the forehead with the device held in a parallel position with the user's facial profile. The conical applicator provides more options regarding targeted facial zones and placement than the flat disk applicators of the prior art. In a particular embodiment, the applicator is about 1.400 inches tall, the vertical length dimension labeled Ht in FIG. 5, and about 0.755 inches in diameter at the base, the horizontal bottom length dimension labeled Dia in FIG. 5. The maximum diameter through the centerpoint in FIG. 6 in the end view is 0.820 inches and is labeled Dia(b) which accounts for the slight bulge at a height of 0.230 inches from the bottom line in FIG. 5, that height labeled Ht(b). From Ht(b), the conical applicator tapers to a point. The applicator of the present invention is thus, relatively small as compared to prior art devices, and enables the user to specifically target areas of the skin, and to get into the contours of the face. In addition, the overall shape of the present invention enables the device to be handled in a wand-like fashion which is more comfortable, intuitive, and precise for most users who will likely be familiar with other wand-like cosmetic applicators. The wand-like handling and the device shape resting in the palm of the hand presents an advantageous look and feel from the flat disk applicator that projects 90° from a bulky handle.

Figure 7A:
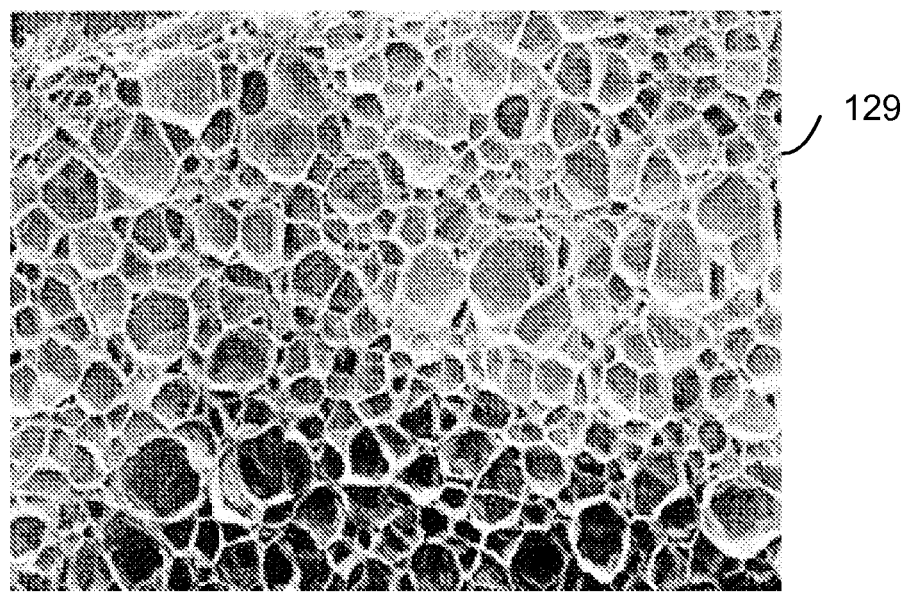
FIG. 7A is a magnified photograph showing the pore structure of a suitable foam material for the foam applicator.
Figure 7B:
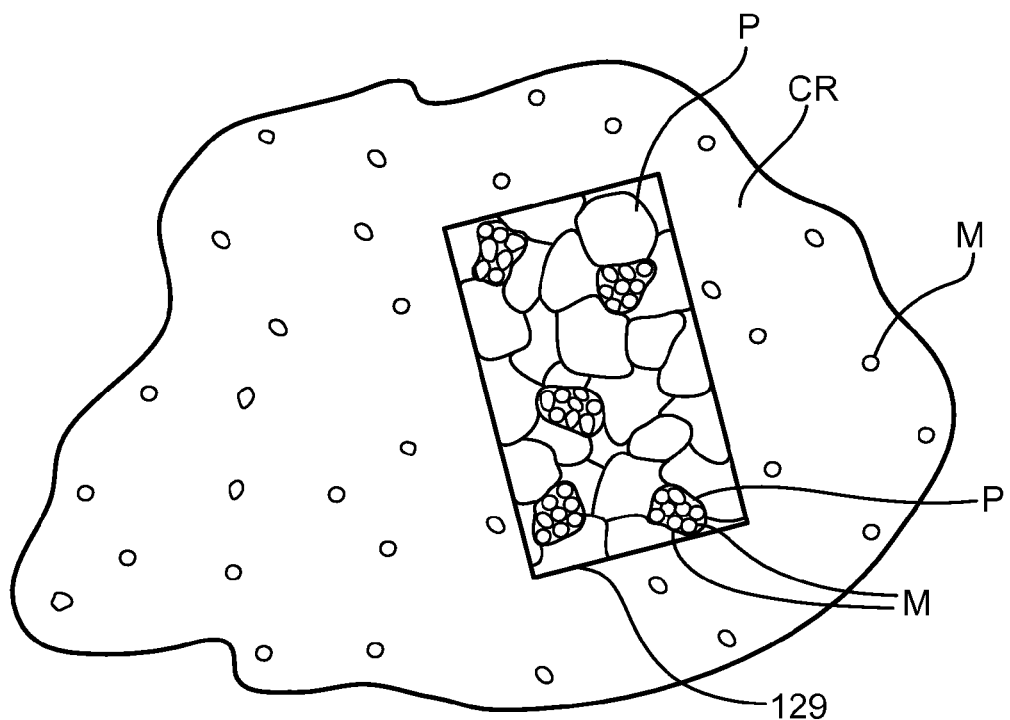
FIG. 7B is a schematic drawing of the foam applicator and a personal care composition with particulate material showing the interaction between the foam structure and the particulate material.

FIG. 7A is a magnified photograph of the pore structure of a suitable foam material 129 for the foam applicator. In developing the invention, different foams were tested and it was determined that the foams should be evaluated on the basis of four parameters: texture, firmness, porosity and cell structure. These parameters are more meaningful in light of one of the advantageous findings of the present invention: the physical interaction between the foam applicator material and the size of the particles in the cream. The porosity and cell structure were chosen to provide the most beneficial interaction between the particles and the foam applicator. Namely, to have the particles held to some degree by the foam to enhance the abrasive action of the skin treatment device. The size of the particles was also optimized by testing to determine which sizes felt adequate for skin polishing and which sizes were too fine to provide substantial benefit and also which sizes were so large that they may irritate the skin. As described below with respect to the test results, an acceptable foam material for the applicator in a preferred embodiment has a porosity ranging from between 65 pores per inch to 120 pores per inch. With regard to firmness, an accurate measure is defined in ASTM protocol D 3574-05 which outlines the Indentation Force Deflection Test or IFD Test. The IFD measurement is another way to express the preferred firmness of the foam applicator material. The result is reported in pounds per square inch (psi) and the IFD test can be conducted at 25% deflection or 65% deflection. In certain embodiments, the applicator 102 is constructed from foam with an IFD at 25% of about 0.5 psi to about 0.8 psi. Foams with higher IFD measurements were too soft, that is, the foam deformed excessively during use; and foams with lower IFD measurements were too hard, that is, the overall sensation was too abrasive as the foam did not cushion the skin adequately.

In certain embodiments, the applicator 102 may be constructed from an open or closed cell foam material such as polyethylene, reticulated ester polyurethane, reticulated ether polyurethane, polypropylene foam, crosslinked polyethylene foam, and ethylene/vinyl acetate copolymer foam. The foam material shown in FIG. 7A is a crosslinked polyethylene open cell foam that meets the porosity and IFD criteria. Specifically the porosity is about 85 pores per inch which provides an average calculated pore diameter of about 0.061 inch. The firmness was measured as 0.7 N+/−0.1N on the IFD test.

The device illustrated in FIG. 4 provides a rotational motion to applicator 102 via the output shaft of the motor. The results of a test described below bear out the conclusion that rotating motion of the conical shaped foam applicator provided better results than prior art devices which employ vibratory motion at the applicator. Rotational motion of the conical applicator means that the motion of the head is parallel to the face. That is, a constant linear velocity is imparted to skin across the head as compared to a vibratory motion which is perpendicular and parallel to the skin.

Figure 8:
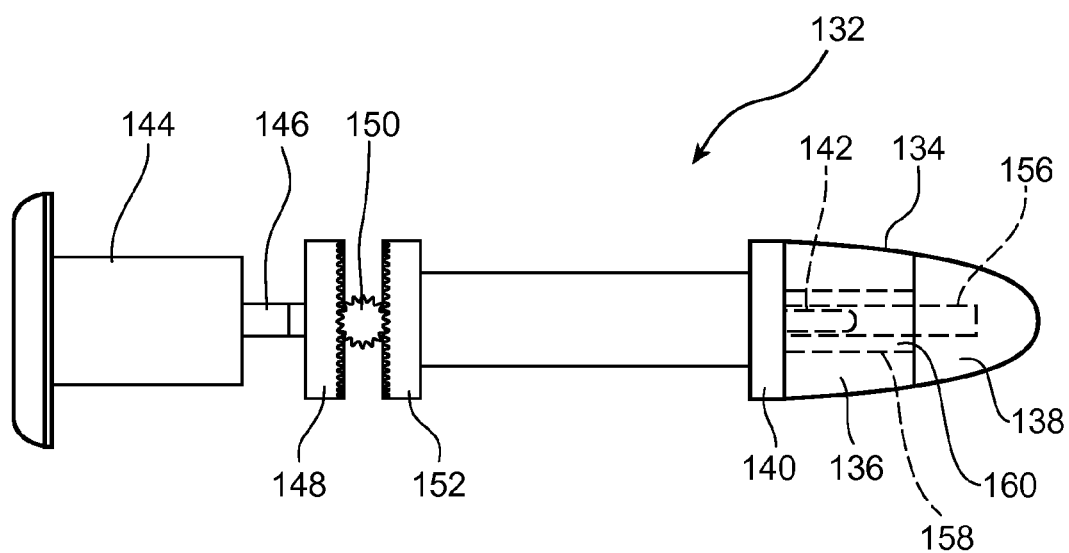
FIG. 8 is a side elevational view of the internal components of an alternative embodiment of the skin treatment device having counter-rotating surfaces.
Figure 9:
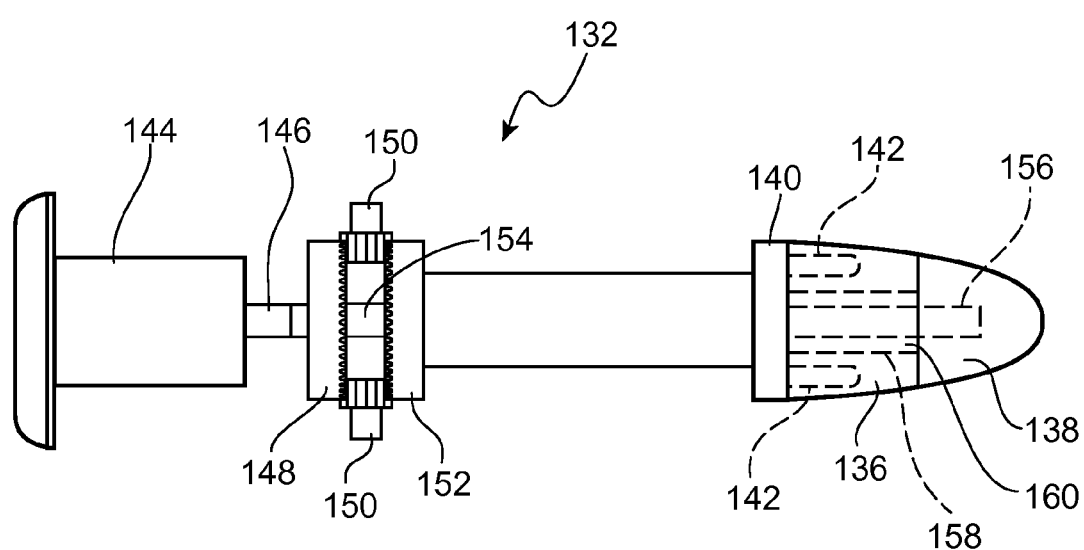
FIG. 9 is front elevational view of the assembly shown in FIG. 8.

Another embodiment of the treatment device is shown in FIGS. 8-9 in which device 132 has an applicator 134 divided into a lower portion 136 and an upper portion 138 mounted on an attachment 140. The portions of applicator attachment 140 that are hidden by the applicator 134 are shown in broken lines and comprise a pair of mounting rods 142 disposed in diametric opposition to one another on the attachment platform. Mounting rods 142 engage internally formed mating areas of the applicator and hold the applicator onto the attachment platform. Skin treatment device 132 has internal structure that enables lower portion 136 and upper portion 138 to counter-rotate relative to one another to provide enhanced microdermabrasion. The counter-rotation is achieved by a gear mechanism contained in the housing. FIGS. 8-9 illustrate schematically the internal elements of device 132 in which a motor 144 has an output shaft 146 extending therefrom. Output shaft 146 may be coupled with a first mechanism such as a first gear 148 which rotates in the same direction as the output shaft. First gear 148 is the driving gear in the arrangement. First gear 148 is a crown-type gear having its teeth on a planar surface instead of the circumferential surface. Output shaft 146 may be coupled with a second mechanism such as a second gear 152 that rotates in a direction opposite of the output shaft. The second gear 152 may be meshed with and driven be a pair or cross gears 150 that are coupled to the first gear 148. Second gear 152 is the driven gear in the arrangement. Second gear 152 is also a crown-type gear with its teeth facing the teeth of first gear 148. As seen in the figures, first gear 148 has a first gear output shaft 154 which is in axial alignment with motor output shaft 146. First gear output shaft 154 extends axially through the housing and through the center of applicator attachment 140 to its free end 156. As shown in dashed lines, free end 156 is surrounded by upper portion 138 of the applicator, and is engaged thereto by any well known means. First gear output shaft 154 by its free end 156 therefore rotates upper portion 138.

The cross gear arrangement enables second gear 152 to counter-rotate with respect to first gear 148. Cross gears 150 transmit the rotational energy of first gear 148 to second gear 152 in the opposite rotational direction. Second gear output shaft 158 is a cylindrical boss that concentrically surrounds first gear output shaft 154. Second gear output shaft 158 is axially aligned with first gear output shaft and the motor output shaft as well. Second gear boss 158 extends through applicator attachment platform 140 such that lower portion 136 of the applicator surrounds and is engaged to output shaft 158. Free end 160 of second gear output shaft 158 is configured to coincide with the division between the upper and lower portions of the applicator such that first gear output shaft extends beyond free end 160 of second gear output shaft 158. Lower portion 136 of the applicator thus rotates in an opposite direction from upper portion 138 of the applicator. This counter-rotating action of the two portions of the applicator enhances the microdermabrasion, polishing, and personal care composition delivery effects of the skin treatment device and prevents the "walking" or forced movement of the head relative to the skin which can happen with a single direction rotational motion. The counter-rotating motion counteracts the "walking" by compensating one rotation motion with the opposite one.

Although conventionally appearing gear teeth are illustrated, the invention is in no way limited to these schematic depictions of the gear mechanism. For example, the gears may be helical or beveled gears which may be particularly advantageous in the cross-gear arrangement. Conventional crown gears may be employed with pointed teeth meshing with mating cross gears.

In several embodiments of the present invention, the device 100 is used in combination with a personal care composition. The skin care composition may improve the efficacy of the device's mechanical microdermabrasion or skin polishing; alternatively, the device may improve the delivery of personal care composition. The personal care composition of the present invention may be a skin care, cosmetic, or hair care product. The personal care composition may be used as, for example, a moisturizer, a conditioner, an anti-aging treatment, a skin lightening treatment, a sunscreen, a sunless tanner, and combinations thereof. The personal care compositions may comprise a dermatologically acceptable carrier. The phrase "dermatologically-acceptable carrier", as used herein, means that the carrier is suitable for topical application to the keratinous tissue, has good aesthetic properties, is compatible with any additional components of the personal care composition, and will not cause any untoward safety or toxicity concerns. The carrier can be in a wide variety of forms. Non-limiting examples include simple solutions (water or oil based), emulsions, and solid forms (gels, sticks, flowable solids, amorphous materials). In certain embodiments, the dermatologically acceptable carrier is in the form of an emulsion. Emulsion may be generally classified as having a continuous aqueous phase (e.g., oil-in-water and water-in-oil-in-water) or a continuous oil phase (e.g., water-in-oil and oil-in-water-in-oil). The oil phase of the present invention may comprise silicone oils, non-silicone oils such as hydrocarbon oils, esters, ethers, and the like, and mixtures thereof. For example, emulsion carriers can include, but are not limited to, continuous water phase emulsions such as silicone-in-water, oil-in-water, and water-in-oil-in-water emulsion; and continuous oil phase emulsions such as water-in-oil and water-in-silicone emulsions, and oil-in-water-in-silicone emulsions.

The personal care composition may comprise a safe and effective amount of one or more skin care active ("active") useful for regulating and/or improving skin condition. "Safe and effective amount" means an amount of a compound or composition sufficient to induce a positive benefit but low enough to avoid serious side effects (i.e., provides a reasonable benefit to risk ratio within the judgment of a skilled artisan). Suitable actives include, but are not limited to, vitamins (e.g., B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (pro-vitamin A); vitamin E compounds, or tocopherol, including tocopherol sorbate, tocopherol acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), peptides (e.g., peptides containing ten or fewer amino acids, their derivatives, isomers, and complexes with other species such as metal ions), sugar amines (e.g., N-acetyl-glucosamine), sunscreens, oil control agents, tanning actives, anti-acne actives, desquamation actives, anti-cellulite actives, chelating agents, skin lightening agents, flavonoids, protease inhibitors (e.g., hexamidine and derivatives), non-vitamin antioxidants and radical scavengers, hair growth regulators, anti-wrinkle actives, anti-atrophy actives, minerals, phytosterols and/or plant hormones, tyrosinase inhibitors, anti-inflammatory agents, N-acyl amino acid compounds, antimicrobials, antifungals, and derivatives of any of the aforementioned actives. The term "derivative" as used herein refers to structures which are not shown but which one skilled in the art would understand are variations of the basic compound. For example, removing a hydrogen atom from benzene and replacing it with a methyl group. Suitable actives are further described in U.S. application publication No. US2006/0275237A1 and US2004/0175347A1.

The personal care composition may comprise a particulate material. Particles can range from mildly abrasive polymeric microbeads to moderately abrasive materials such as sodium bicarbonate to relatively aggressive materials such as alumina crystals. Particulate materials suitable for use herein include but are not limited to bismuth oxychloride, sericite, mica, mica treated with barium sulfate or other materials, zeolite, kaolin, silica, boron nitride, lauroyl lysine, nylon, polyethylene, talc, polypropylene, polystyrene, ethylene/acrylic acid copolymer, sericite, aluminum oxide, silicone resin, barium sulfate, calcium carbonate, cellulose acetate, PTFE, polymethyl methacrylate, starch, modified starches such as aluminum starch octenyl succinate, silk, glass, fibers, ground seeds, pumice, interference pigments, and mixtures thereof.

The particulate material may have an average primary particle size from about 90 microns to about 600 microns. In other embodiments, the particulate material may have an average primary particle size from about 150 microns to about 500 microns. In other embodiments, the particulate material may have an average primary particle size from about 200 microns to about 400 microns. Testing was conducted to gauge the efficacy of several formulations and particle combinations. With regard to particulate size, participants preferred polypropylene beads having an average primary particle size from about 200 μm to about 400 μm. The larger beads may be considered too aggressive for some users. Smaller microbeads are considered too fine to give a substantial benefit. Average primary particle size is typically provided by the supplier of the particulate material. However, the average primary particle size can be analyzed by methods well known to a skilled artisan such as by microscopy analysis.

The personal care composition may comprise from about 0.01% to about 25%, by weight, of the particulate material. In a particular embodiment, the personal care composition comprises from about 1% to about 10%, by weight, of the particulate material. In another embodiment, the personal care composition comprises from about 2% to about 4%, by weight, of the particulate material. Testing was conducted to determine the efficacy of various weight percentages of particulate material (i.e., polymeric microbeads with an average primary particle size from about 200 μm to about 400 μm). A personal care composition containing 0% microbeads did not fit the concept of a skin polisher, and a personal care composition containing 8% microbeads was considered by may participants as being too rough and too difficult to rinse off. Personal care compositions containing about 2% and about 4% microbead creams were preferred. The 2% example was perceived as creamy, pleasurable, and easy to rinse off but still providing a polishing effect. The 4% example was perceived as providing more of a polishing benefit but was harder to rinse off. The viscosity of the personal care composition may be between about 40,000 cps to about 500,000 cps. In certain embodiments, the personal care composition has a viscosity range of about 50,000 cps to about 200,000 cps. Personal care composition having too low of a viscosity tended to be thrown from the skin when engaged by the rotating applicator of the device. Furthermore, personal care compositions having too low of a viscosity were unable to adhere the particulate material to the applicator which resulted in particulate material being thrown from the skin. Viscosities are measured on a Brookfield viscometer using an appropriate T-bar spindle at 5 rpm at 25° C.

The personal care composition may further comprise a colorant. Suitable colorants may include inorganic or organic pigments and powders. Organic pigments can include natural colorants and synthetic monomeric and polymeric colorants. Organic pigments include various aromatic types such as azo, indigoid, triphenylmethane, anthraquinone, and xanthine dyes which are designated as D&C and FD&C blues, browns, greens, oranges, reds, yellows, etc. Organic pigments may consist of insoluble metallic salts of certified color additives, referred to as the Lakes. Inorganic pigments include iron oxides, ferric ammonium ferrocyanide, manganese violet, ultramarines, chromium, chromium hydroxide colors, and mixtures thereof. The pigments may be coated with one or more ingredients that cause the pigments to be hydrophobic. Suitable coating materials that will render the pigments more lipophilic in nature include silicones, lecithin, amino acids, phospholipids, inorganic and organic oils, polyethylene, and other polymeric materials. Suitable silicone treated pigments as disclosed in U.S. Pat. No. 5,143,722. Inorganic white or uncolored pigments include TiO2, ZnO, or ZrO2, which are commercially available from a number of sources. Other suitable colorants are identified in U.S. Pat. No. 7,166,279. Colorants are generally included at a weight percent such that the personal care composition yields a perceptible color. In one embodiment, the personal care composition exhibits a color that perceptibly different from the color of the applicator. By perceptibly different, refers to a difference in color that is perceptible to a person having normal sensory abilities under standard lighting conditions (e.g., natural illumination as experienced outdoors during daylight hours, the illumination of a standard 100 watt incandescent white light bulb at a distance of 2 meters, or as defined by CIE D65 standard illuminate lighting at 800 lux to a 1964 CIE standard observer).

As described above, the parameters for selecting the foam material for the applicator and the concentration and sizes of microbeads in the personal care composition were determined to provide a degree of interaction between the microbeads and the cell structure of the foam. As shown schematically in FIG. 7B in which personal care composition CR is depicted containing an more or less even distribution of microbeads M, a magnified portion of foam material 129 shows that a number of microbeads M get trapped in a pore P of the foam material. This schematic depiction relies on the preferred ranges of sizes of the pores and microbeads as described above. In other words, a porosity of 85 pores per inch results in an average measured pore size of about 0.061 inch. This dimension converts metrically to 1,549 µm. Given that a suitable microbead size is about 200 µm, this means that each average sized pore will trap between 7-8 microbeads. The firmness range chosen for the foam material ensures that the foam will cushion the microbeads somewhat to provide a suitable skin polishing effect without irritating the skin. The microbeads are trapped within the pore structure of the foam such that they do not fly off during use and provide the desired abrading effect. In certain embodiments, the applicator 102 may comprise particulate material such as microbeads disposed on the outer surface of the applicator. The particulate material may be disposed on the applicator by conventional means (e.g., with an adhesive or by embedding the particulate material into the material forming the applicator 102). Such embodiments are believed to provide an exfoliation or skin polishing benefit without the need for a separate skin care composition. In a particular embodiment, the particulate material is disposed is the pores of a foam applicator.

The effect of the combination of the foam material and particles with rotational motion of the foam tip was tested and compared with a prior art applicator that provides vibratory motion on a flat disk shaped applicator. Among the conclusions from the study were that (i) a rotating conical shaped applicator with a smaller treatment head was able to perform better exfoliation; and that (ii) the skin treatment device with the personal care composition comprising particulate material such as microbeads performed better than the device alone. The study monitored a control and five different combinations of treatment devices with creams over a 5 day period with the objective of comparing the b values of the skin of the subjects and the control. The b value is the average of three b value measurements. The b value in skin color is a measure of the yellowness of skin and represents the balance between blue (negative values) and yellow (positive values). The higher the b value, the more yellow is present in the skin. The measurements are taken with a calorimeter and an exemplary test method on which this test was based is described in ASTM E313-05, Standard Practice of Calculating Yellowness and Whiteness Indices from Instrumentally Measured Color Coordinates.

The protocol for the study undertaken entailed gathering the test subjects and staining their forearms on Day 1 of the five-day test with a sunless tanning agent. The analysis of the measured values is shown graphically in FIGS. 10-12. The subjects used the following combinations:
  Example A—subject used only the skin treatment device of the present invention alone without any personal care composition (PCC).
  Example B—subject used the skin treatment device of the present invention with a PCC designated "β"
  Example C—subject used the skin treatment device of the present invention with a PCC designated "α"
  Example D—subject used a prior art treatment device with the PCC designated "β"
  Example E—subject used the same prior art device as in Example D but with the PCC designated "α"
  Example F—subject was the control whose skin was stained but not treated throughout the 5 day period.

This study focused mostly on the motion of the skin treatment device applicator and the foam material. The prototype employed resembled the device illustrated in FIGS. 1-6 with a single piece foam applicator the entirety of which rotated in a single direction to provide consistent linear velocity along the foam applicator. The prior art device employed in the study was a conventional vibratory device with a flat disk shaped head in which the handle is at a 90° angle with respect to the applicator head. Both personal care compositions designated α and β are prior art exfoliating creams currently available on the market.

Figure 10:
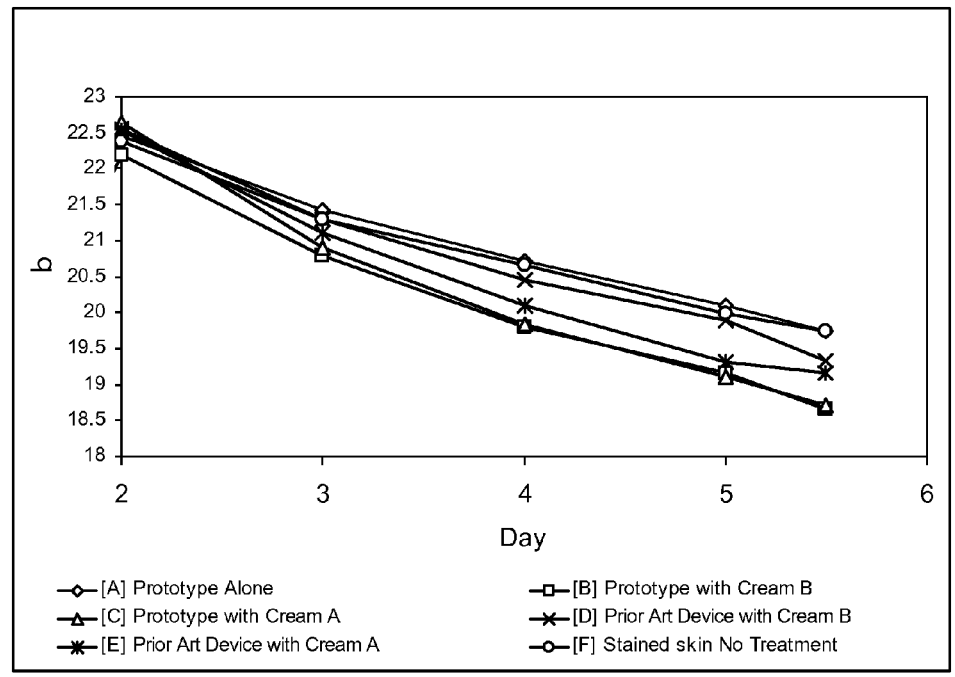
FIG. 10 is a plot of the b values for Days 2-5 of the skin lab study.

The b values were obtained on Day 2 of the test and represent the baseline, FIG. 10. Prior to treatment, b value readings were taken on Days 3-5. On Day 5, the subjects returned to the test site for a final b value reading. This final b value reading is represented by the Day 5.5 data points in FIGS. 10-12. A lower b value represents a higher degree of exfoliation or skin polishing, so in this context, a lower b value demonstrates better performance. Referring to FIG. 10, the b values for Days 2-5 are plotted, and there is significant evidence to conclude that the skin treatment device of the present invention used with a personal care composition, Examples B and C, is significantly different from the other treatments. On Days 3 and 4, both the prior art device and the present invention used with a personal care composition, Examples B, C and E, provided significant differences from the other treatments. On Day 5, the present invention used with a personal care composition, Examples B and C, is significantly different from the other treatments.

Figure 11:
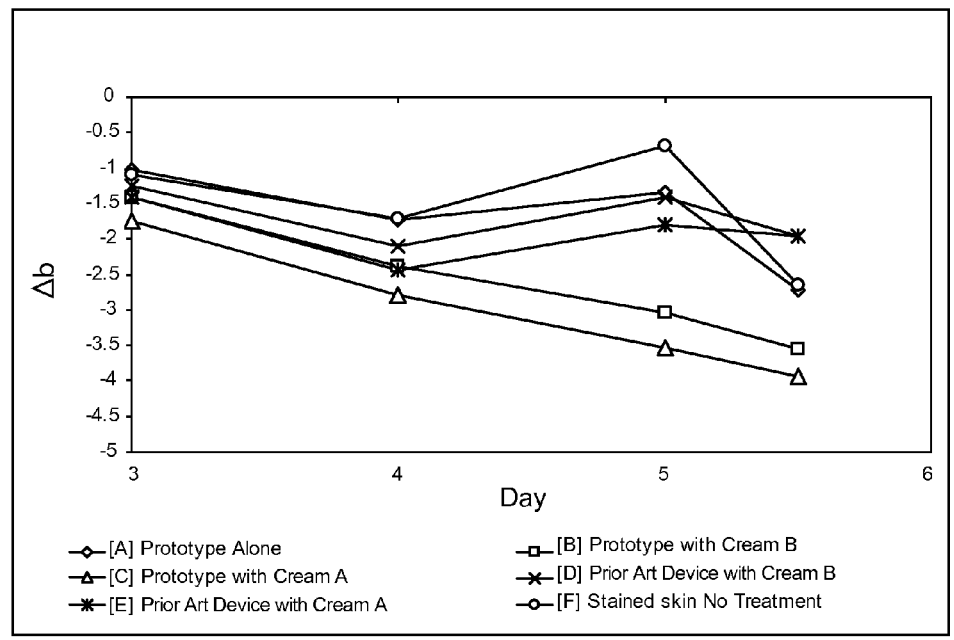
FIG. 11 is a plot of the change in b values from a baseline over the same days.

FIG. 11 is a plot of the Δb value from the baseline measurement on Day 2. The top of the y-axis is zero, so in this context, the more negative values indicate better performance. As seen in FIG. 11, the use of the present invention plus a personal care composition, Examples B and C, show an almost linear plot and represent the most significant changes from the baseline, ranging from about −1.3 to −4.0. As might be expected, the Δb value of untreated skin show the least amount of change until up until Day 5. The prior art device with personal care composition, Examples D and E show a somewhat sawtooth plot that ranges between −1.0 to −2.5.

Figure 12:
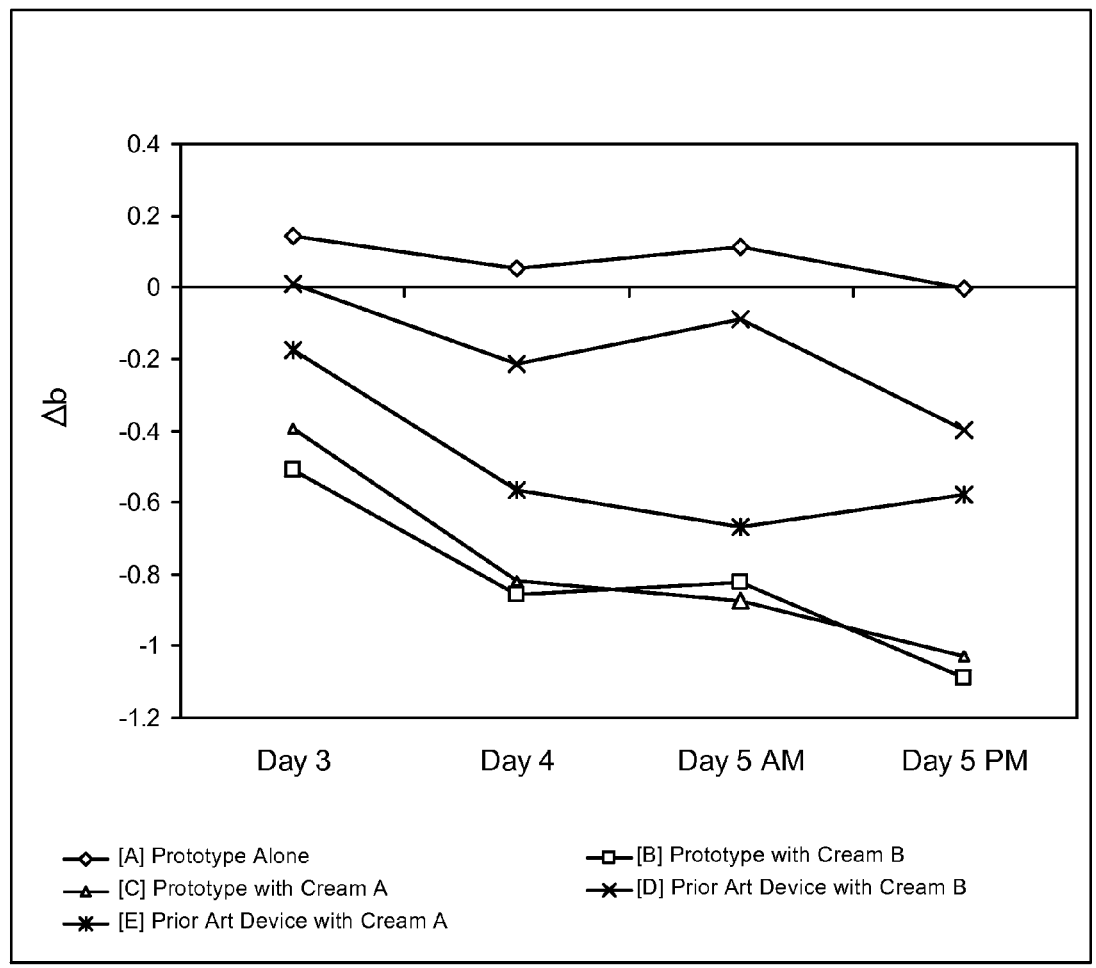
FIG. 12 is a plot of the change in b values from the control over the same days.
Figure 13:
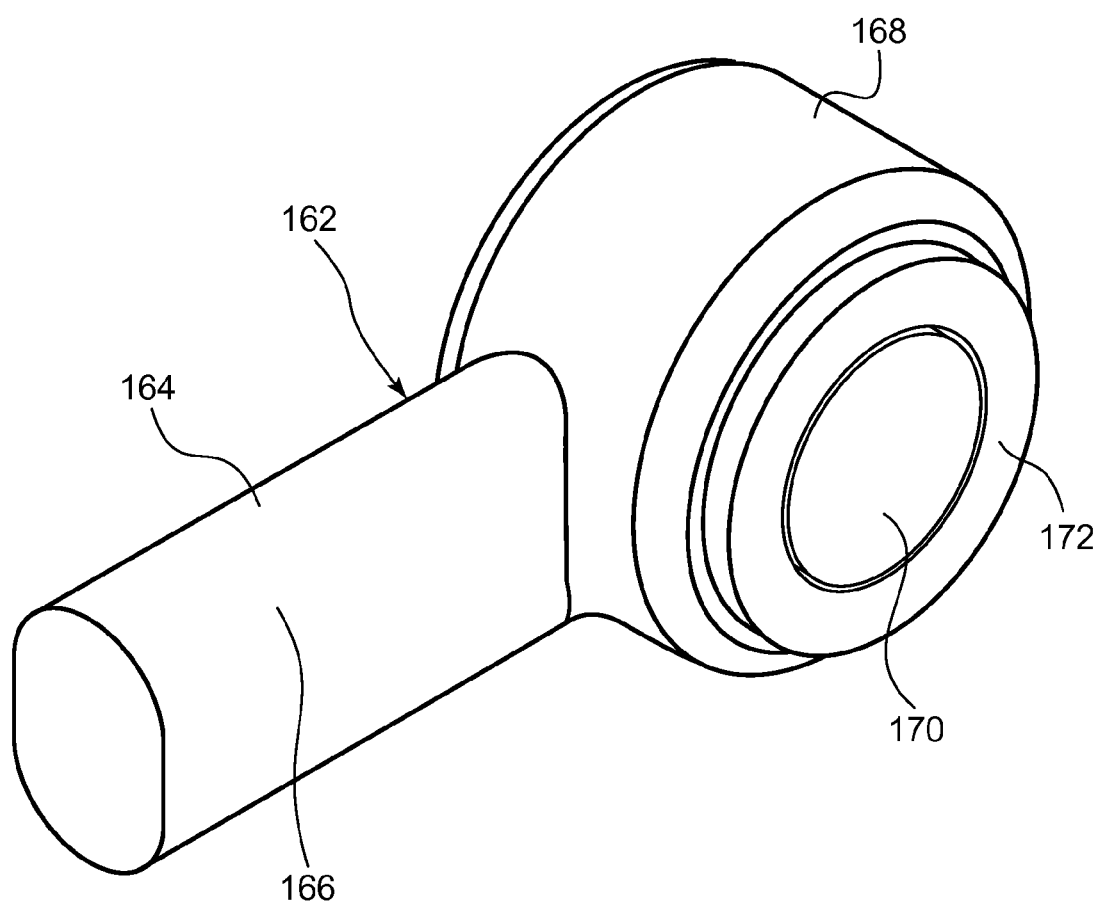
FIG. 13 is a perspective view of a skin treatment device of an alternative embodiment.

FIG. 12 is a plot of Δb value compared to the control, Example F, over the same five day period. This plot shows that again, the present invention with personal care composition, Examples B and C, provided larger changes in b values over time and represent the most negative data points. The study demonstrates that the skin treatment device of the present invention, even when used with prior art personal care composition, provided the best performance as compared to the prior art device.

The study whose results are graphed in FIGS. 10-12 use a tinted patch of skin on the forearms of the subjects. Another test that could be conducted to demonstrate the superior performance of the present invention compared to the prior art in reaching crevices and contours is one in which identical artificial human heads are painted in the transition crevice between the nose and cheek with colored mascara or other material offering high contrast with skin. The skin treatment device of the present invention with the conical applicator is used to remove the mascara on one face, and the prior art device having a flat disk shaped applicator is used to remove the mascara from another face. Based on the geometric shape and dimensions of the conical shape of the present invention, it will more thoroughly remove mascara from the crevice as compared to the flat disk shaped applicator of the prior art. The removal of mascara represents the reach of the applicator in exfoliating or polishing the skin in that contoured area of the face.

The personal care composition may be disposed in any suitable container that may contain a unit dose (i.e., a single dose of the personal care composition which is to be completely dispensed and applied) or bulk quantity (i.e., multiple doses of the personal care composition) of the personal care composition. Suitable containers include jars, bottles, vials, ampules, pouches, cans, carton, canisters, capsules, tubes, blister packs, and like devices. In certain embodiments the personal care composition may be embedded in the applicator. For example, the personal care composition may be in the form of a lotion or cream that is embedded into the foam applicator. Such an embodiment provides the user with an applicator pre-loaded with the ideal quantity of personal care composition, which avoid ineffectiveness caused by using too little composition and inefficiency caused by using too much composition.

The skin treatment device of the present invention, in addition to having the particular geometric shape of the device as a whole and the conical shape of the applicator and presenting advantageous materials for the applicator also is equipped with more ergonomic and safety features. One feature is an indicator of some type that informs the user that the particular area has undergone a suitable amount of microdermabrasion or polishing. There are a number of possible ways of providing the user with an indicator. Chief among them being a timer that automatically shuts off the motor; or a color change to the microbeads or topical. In certain embodiments, the timer mechanism may be programmed in PCB to shut off the motor after a certain time lapse from it being turned on. This will prevent the user from over-abrading the skin. More subtle but just as useful if not more from an ergonomic standpoint, this will enhance the use experience by giving the user certainty in knowing that a suitable degree of exfoliation has taken place. A signal that tells the user there is a finish line to the skin treatment process will be a welcome benefit.

Another safety feature is a torque limiter. Any element that rotates generates torque, and the amount of torque in the context of the present invention would be affected by a number of factors including the position of the applicator, the amount of cream it is carrying or the amount of pressure impinging the applicator to the skin. The torque limiter enhances the safety of the device by ensuring that a user will not be able to exceed an acceptable level of abrasive pressure against the skin. The torque limiter would be designed to be triggered at a predetermined torque. Triggering can be carried out in a number of ways ranging from providing an indicator or signal to the user that a condition exists that needs to be resolved for continued use of the device to shutting down the motor or decoupling the applicator from the output shaft to stop the action of the applicator altogether. For example, the torque limiter may simply stall the motor when a threshold torque is achieved which informs the user that they need to change the position of the device or decrease the amount of pressure against the skin. Alternatively, when a threshold torque is exceeded, the torque limiter operates to decouple the applicator from the output shaft, or deactivate the motor or a combination thereof. An example of a mechanical torque limiter is a magnetic coupling that is coupled to the motor or output shaft and the applicator attachment. With this type of mechanism, when the torque applied via the applicator reaches or exceeds a predetermined allowable torque, the magnetic coupling disconnects the drive from the applicator attachment. An electronic version of a torque limiter could be created by programming a component on the PCB to deactivate the motor when the torque applied via the applicator reaches or exceeds the predetermined allowable level.

In the skin treatment device of the present invention, the maximum torque for the device is a variable that depends on the abrasiveness of the applicator and the particulate containing personal care composition. For the particular applicator material and microbead containing personal care composition employed in the studies, the maximum torque was 20 mNm. For a less abrasive combination of applicator material and microbead containing personal care composition, this number would increase, and for a more abrasive combination this number would decrease. An acceptable range of predetermined maximum allowable torques for the present invention may be between approximately 20 mNm to 40 mNm depending on the foam and cream combination. At these threshold torque levels, the applicator would be stalled by deactivation of the motor or decoupling from the output shaft.

Another feature of the present invention is the sanitation and convenience of a disposable applicator 102. As any user of cosmetic sponge or foam materials can attest, once these materials are impregnated with a cream or lotion, it is very difficult to clean. Also, as a health concern, applicators 102 should may either harbor or spread harmful bacteria and fungi. Once the applicator 102 is used once, it may become contaminated and the use may desire a "fresh" applicator 102 with each use. Some dermatological conditions are notoriously difficult to manage, and re-using contaminated foam applicators increases the likelihood of continued infection. This is particularly true if multiple users share the device. In some embodiments of the present invention, the applicator 102 is intended for a single use. The applicator 102 may be removed from the device after use. In certain embodiments, the device may be designed to enable the user to remove the applicator 102 without touching it with the hands. The applicator ejection control 116 enables for easy removal and disposal of the foam material from the device directly into an appropriate waste container.

The replacement applicators may be provided in a user-friendly package. In one embodiment, replacement applicators may be provided in a cartridge-type package to ensure that they are isolated from one another to maintain their sterility and to facilitate attachment to the device. In another embodiment, replacement applicators may be individually wrapped or sealed to preserve cleanliness. Suitable packaging includes, but is not limited to, blister-packs and foil or film pouches/sachets.

Referring now to FIGS. 13-16 an alternative embodiment of a skin treatment device 164 is illustrated which comprises a housing 164 including a handle 166 and a treatment head portion 168. Treatment head portion 168 is cylindrical and presents on one circular face concentric applicator surfaces. The concentric applicator surfaces include an inner treatment surface 170 and an outer treatment surface 172. These treatment surfaces counter-rotate with respect to one another to provide an enhanced microdermabrasion or skin polishing experience. The handle and the treatment surfaces are parallel to one another in contrast to the previously described embodiments in which the handle and the treatment tip are axially aligned with one another.

Figure 14:
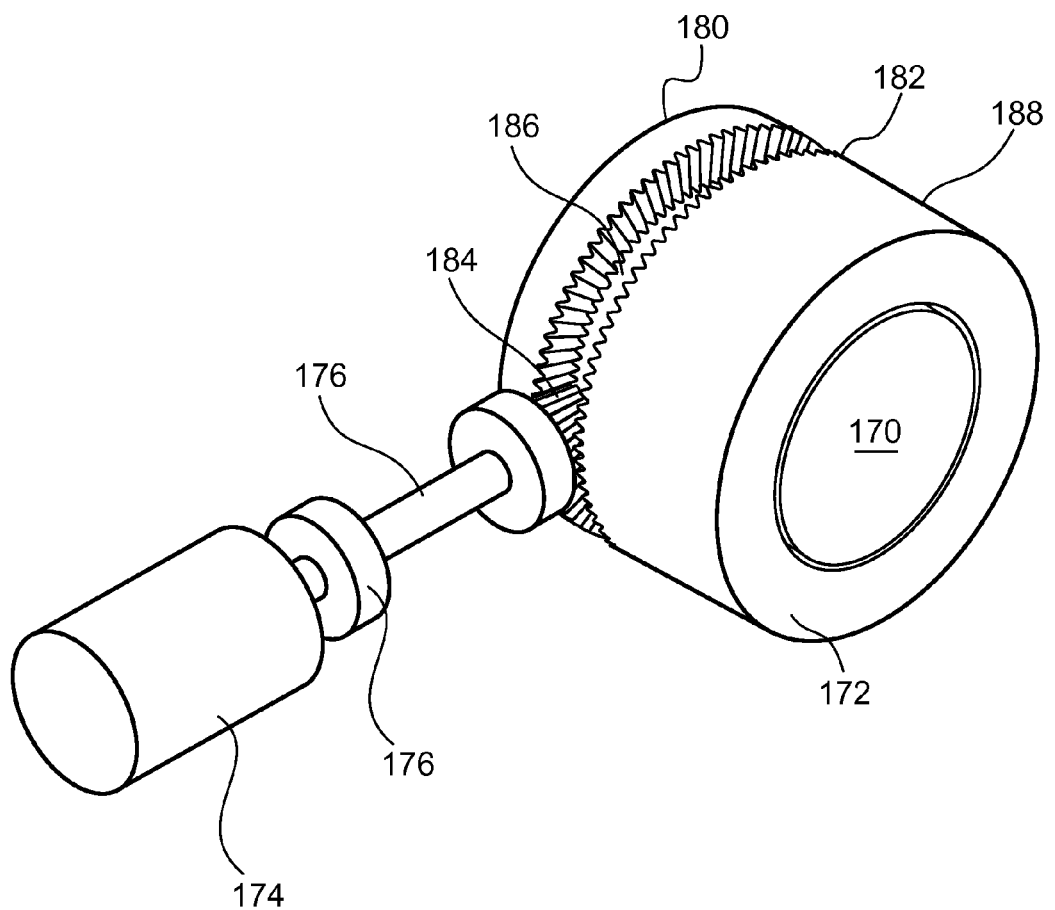
FIG. 14 is a perspective view of the internal structure of the skin treatment device of FIG. 13.
Figure 15:
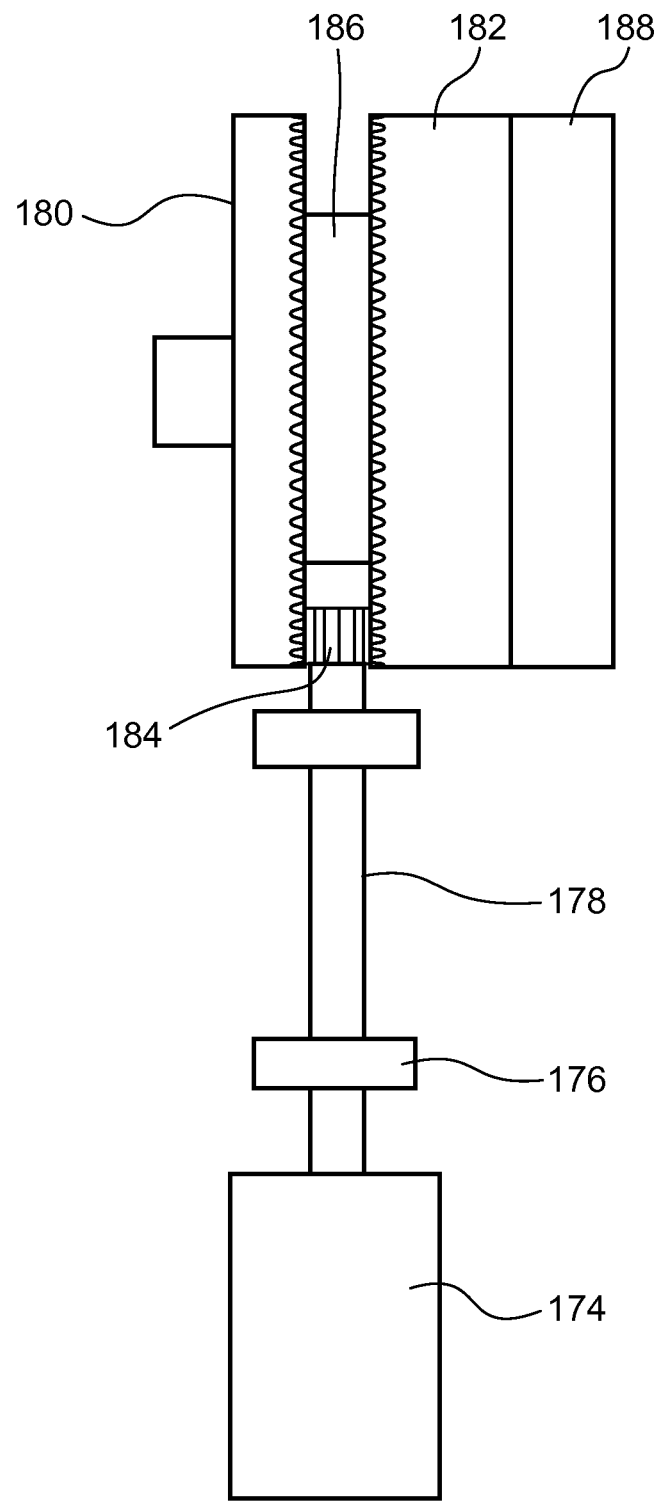
FIG. 15 is a top plan view of the internal structure of FIG. 14.
Figure 16:
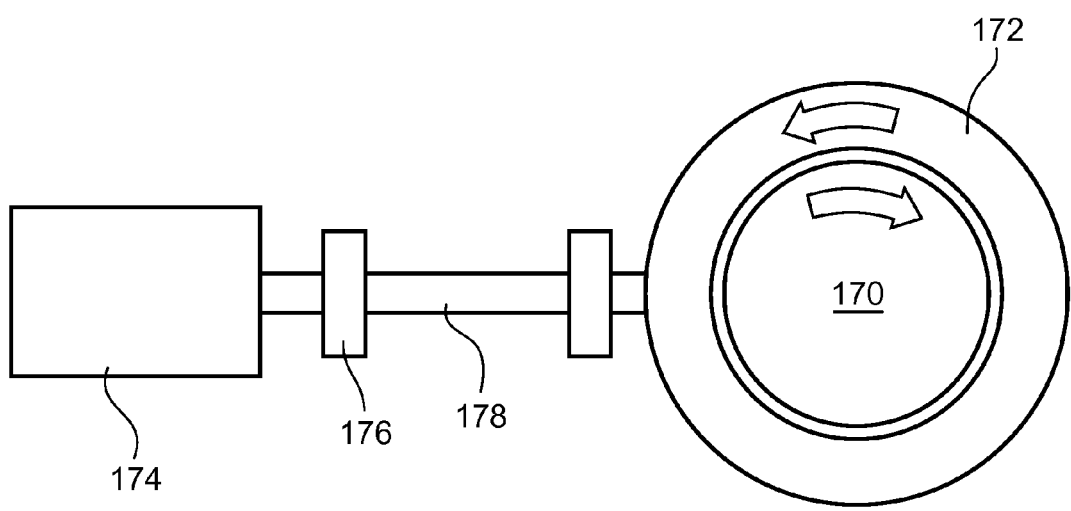
FIG. 16 is an end view of the internal structure of FIG. 14.

The parallel relationship of the treatment surfaces and the handle is made possible by the internal drive mechanism shown schematically in FIGS. 14-16. Internally, a battery 174 provides power to a motor 176 with an output shaft 178. Employing the principles of the gear arrangement of the embodiment of FIGS. 8-9, but configured in a different orientation such that the motion of the output shaft is transmitted to a perpendicular axis, a pair of crown-type gears 180 and 182 are disposed such that the teeth areas face one another. A cross gear 184 is connected to output shaft 178 and is disposed between gears 180 and 182 and meshed with both of them. Cross gear 184 serves as a spur gear and drives both gears 180 and 182 while transmitting the rotation of the output shaft to a perpendicular axis. First gear 180 is coupled to an internal boss 186 which carries inner treatment surface 170. Second gear 182 is coupled to an external boss 188 which carries outer treatment surface 172. Bosses 186 and 188 are axially aligned with one another to provide motion to the counter-rotating treatment surfaces 170 and 172. The directions of rotation are shown by arrows in FIG. 16.

In this embodiment the treatment surfaces of device 162 are provided with an exfoliating substrate such as a special grade non-woven or super-fine grade sandpaper or other like abrasive pads. The sandpaper or abrasive pads are adhered to the treatment head and can be easily removed for disposal. Depending on how the device is sized, the flat treatment surfaces provide an efficient way to treat larger areas of skin such as the arms or legs in contrast to the face. If the device is sized appropriately, device 162 could be used on facial skin as well.

Figure 17:
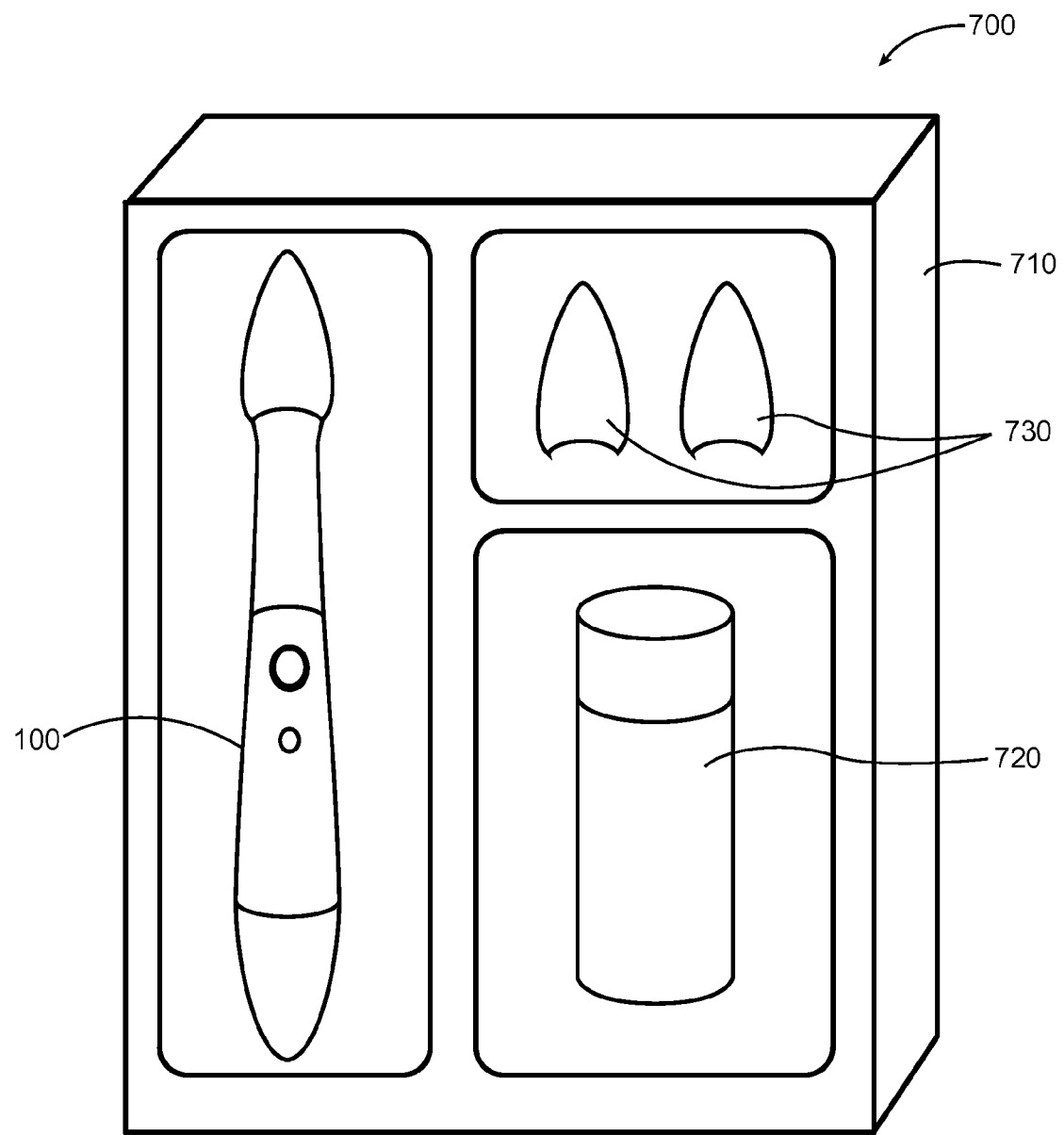
FIG. 17 is a perspective view of a skin treatment kit.

Another aspect of the present invention relates to a skin treatment kit, as shown in FIG. 17. The skin treatment kit 700 may be in the form of a consumer unit 710. A "consumer unit" is a single entity for consumer sale that contains the components of the kit. The consumer unit may comprise several packages, boxes, or other like containers that are joined to form a single entity (e.g., several smaller packages contained within a larger container, several packages bound or adhered to for a single entity, etc.). In certain embodiments, the skin treatment kit 700 comprises any of the aforementioned embodiments of the skin treatment device 100 and any of the aforementioned embodiments of the personal care composition (shown as being contained within a bottle 720). In embodiments where the skin treatment device 100 allows for the replacement of applicators, the kit may further comprise one or more replacement applicators 730. The replacement applicators and/or the packaging of the replacement applicators may be color-coded. The term "color-coded" means that items with different colors (e.g., different colored applicators) have different physical or chemical properties. For example, in one embodiment, the kit may include color-coded applicators wherein differing colors represent differing foam firmness and/or foam porosity. Such a kit may then offer a clear communication to the user that a first color applicator is designed for a first type of user (e.g., sensitive skin) and/or a first area of use (e.g., facial use) and a second color applicator is designed for a second type of user (e.g., normal skin) and/or a second area of use (e.g., hand and foot use).

In other embodiments, the kit may comprise replacement applicators with the personal care composition disposed therein. The kit may comprise a first applicator with a first personal care composition disposed therein and a second applicator with a second personal care composition disposed therein. The first and second personal care compositions may differ in one or more attributes. For example, the compositions may have different particulate material and/or different weight percentages of particulate material. The composition may differ in the dermatologically acceptable carrier (e.g., first composition is a oil-in-water emulsion and the second is a water-in-oil emulsion). The compositions may have different skin actives and/or different weight percentages of skin actives. The replacement applicators with the personal care composition and/or the packaging of the replacement applicators may be color-coded.

The present invention further relates a method for treating the skin. The method of treating the skin conditions comprises the step of topically applying to the skin an effective amount of a personal care composition. The amount of the composition applied, the frequency of application and the period of use will vary widely depending upon the level of components of a given composition and the level of regulation desired. For example, from about 0.01 g composition/$cm^2$ to about 1 g composition/$cm^2$ of keratinous tissue may be applied. In one embodiment, the compositions are applied at least once daily, where "daily" and "days" mean a 24-hour period. For example, the compositions may be applied daily for 30 consecutive days, alternatively for 14 consecutive days, alternatively for 7 consecutive days, and alternatively for 2 consecutive days. The method further comprises applying a skin treatment device having a rotating applicator to the skin for a prescribed period of time. After application of the skin treatment device, a second personal care composition may be applied to treated skin.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A skin treatment kit comprising:
   a) a skin treatment device comprising:
      i) a housing having a handle end extending to a neck portion and an applicator attachment end, said housing containing a battery, a motor adapted to impart a rotary motion to an output shaft when actuated, said output shaft extending through said applicator attachment end and coupled to an applicator shaft portion, and further comprising a power switch for said motor, and
      ii) a conical shaped applicator coupled to said applicator shaft portion of said housing such that the rotary motion of said output shaft is imparted to said applicator wherein the applicator rotates in a direction parallel to the skin being treated;
      iii) a torque limiter to decouple said motor from said applicator when the torque generated at said applicator reaches a predetermined value; and
   b) a personal care composition comprising:
      i) from about 0.01% to about 25%, by weight of the composition, of a particulate material, said particulate material having an average primary particle size from about 90 μm to about 600 μm, and
      ii) a dermatologically acceptable carrier.

2. The skin treatment kit of claim 1, wherein said applicator is formed of a foam having a porosity ranging from 65 pores per inch to 120 pores per inch.

3. The skin treatment kit of claim 1, wherein said applicator is formed of a foam having a firmness ranging from 0.5 psi to 0.8 psi according to the IFD 25% deflection test.

4. The skin treatment kit of claim 1, wherein said applicator is a foam selected from a group consisting of polyethylene foam, reticulated ester polyurethane foam, reticulated ether polyurethane foam, polypropylene foam, crosslinked polyethylene foam, and ethylene/vinyl acetate copolymer foam.

5. The skin treatment kit of claim 1, wherein said skin treatment device further comprises a timer to deactivate said motor after a predetermined time lapse from actuation, wherein said timer is disposed in the housing and is coupled to the motor.

6. The skin treatment kit of claim 1, wherein said skin treatment device further comprises a printed circuit board disposed in said housing and coupled to said motor to control operation of said device.

7. The skin treatment device of claim 6 wherein said printed circuit board includes a timer to deactivate said motor after a predetermined time lapse from actuation.

8. The skin treatment kit of claim 1, wherein said skin treatment device further comprises an applicator ejection control to facilitate removal of said applicator from said housing.

9. The skin treatment kit of claim 1, wherein said battery and said motor are in axial alignment.

10. The skin treatment kit of claim 1, wherein said personal care composition comprises from about 1% to about 10%, by weight of the composition, of the particulate material.

11. The skin treatment kit of claim 1, wherein said personal care composition exhibits a viscosity of about 40,000 cps to about 500,000 cps.

12. The skin treatment kit of claim 11, wherein said personal care composition exhibits a viscosity of about 50,000 cps to about 200,000 cps.

13. The skin treatment kit of claim 1, wherein said personal care composition further comprises a skin care active selected from a group consisting of vitamins, peptides, sugar amines, sunscreens, skin lightening agents, flavonoids, protease inhibitors, N-acyl amino acid compounds, derivatives thereof, and combinations thereof.

14. The skin treatment kit of claim 1, wherein the personal care composition is embedded in the applicator.

15. The skin treatment kit of claim 1 further comprising one or more replacement applicators.

* * * * *